United States Patent
Sanchez-Zambrano

(10) Patent No.: US 6,654,644 B2
(45) Date of Patent: Nov. 25, 2003

(54) PACEMAKER ELECTRODE

(76) Inventor: Sergio Sanchez-Zambrano, 811 N. Main, Cleburne, TX (US) 76031

( * ) Notice: Subject to any disclaimer, the term of this patent is extended or adjusted under 35 U.S.C. 154(b) by 0 days.

(21) Appl. No.: 09/891,998

(22) Filed: Jun. 26, 2001

(65) Prior Publication Data

US 2003/0023293 A1 Jan. 30, 2003

(51) Int. Cl.$^7$ ................................................. A61N 1/05
(52) U.S. Cl. ..................................................... 607/122
(58) Field of Search ................... 607/119–132

(56) References Cited

U.S. PATENT DOCUMENTS

| | | | |
|---|---|---|---|
| 4,721,118 A | * | 1/1988 | Harris ........................ 607/128 |
| 4,841,971 A | | 6/1989 | Hess |
| 6,241,726 B1 | | 6/2001 | Chia et al. |

* cited by examiner

Primary Examiner—Scott M. Getzow
(74) Attorney, Agent, or Firm—Bracewell & Patterson, L.L.P.

(57) ABSTRACT

An extractable endocardial tip for an electrode of an electrical stimulator has a lead body with a front end for positioning the electrode within a desired area and a back end for connecting to an electrical source. At least one fin protrudes from the lead body. The fin having an anterior leading edge and a posterior receding edge wherein the posterior receding edge is serrated to form a cutting surface. The serrated cutting edge is relatively sharp such that when the electrode is pulled, the serrated edge cuts through any fibrous scar tissue or any other material that surrounds the electrode to facilitate the relatively easy withdraw of the electrode from the heart. Further, the cutting edge re-cuts the original opening allowing for later reinsertion of a new lead through the same opening. The lead body may have convexities or concavities to increase the contact surface area and improve conductivity.

17 Claims, 3 Drawing Sheets

PACEMAKER ELECTRODE

BACKGROUND OF THE INVENTION

1. Technical Field

The present invention is directed to electro-stimulators and a pacemaker electrode, and specifically for the removal of implanted endocardial pacemaker electrodes from a patient's heart and the venous paths thereto.

2. Description of the Related Art

Various types of pacemaker leads and their electrodes are used in different chambers of the heart, including the right ventricle, right atrial appendage, the atrium and the coronary sinus. The leads provide an electrical pathway between a pulse generator, connected to the proximal end of the lead, and the electrode connected to the distal end of the lead. The electrode tip is often placed in contact with the endocardial or myocardial tissue by passage through a venous access, such as the subclavian vein or one of its tributaries, which leads to the endocardial surface of the heart chambers. The electrode tip of many available leads include flexible tines, wedges or finger-like projections which project radially outward to help prevent dislodgment of the lead tip from the cardiac tissue. Once an endocardial lead is implanted within a heart chamber, the bodys reaction to its presence furthers its fixation within the heart. Shortly after placement, blood clots form about the electrode due to enzymes released in response to the irritation of the cardial tissue caused by the electrode tip. Over time, fibrous scar tissue eventually forms over the distal end, usually in three to six months. Electrical pulses emitted by the pacemaker travel through the pacemaker lead, to the electrode and into the heart muscle and stimulate the heart to restore healthy heart rhythms for patient's whose hearts are beating irregularly.

Leads and electrode tips occasionally malfunction, due to a variety of reasons, including lead block, insulation breaks, breakage of the inner helical coil conductor, etc. In addition, it is sometimes desirable to electronically stimulate different portions of the heart than that being stimulated with electrode tips already in place. Due to these and other factors, a considerable number of patients may eventually have more than one, and sometimes as many as four or five, unused leads and electrode tips in their venous systems and heart. These unused leads and electrode tips often develop complications, such as valvular regurgitation, infection, septicemia, or endocarditis. In addition, unused leads may entangle over time, thereby increasing the likelihood of blood clot formation, which may embolize to the lung and produce severe complications or even fatality. Further, the presence of unused leads in the venous pathway and inside the heart may cause considerable difficulty in the positioning and attachment of new endocardial leads and electrode tips in the heart.

Conventional techniques for removing unused pacemaker leads and electrode tips are associated with serious risks. Standard mechanical traction and, more often, intravascular mechanical countertraction are the methods most commonly used at present. External mechanical traction involves grasping the proximal end of the lead and pulling. This process is repeated daily and usually a few millimeters of the lead are removed from the patient each day, with progress monitored by chest radiography. Internal mechanical traction is accomplished by exerting traction (manual or sustained) on the lead via a snare, forceps or other retrieval catheter that has grasped the lead within the venous system. These techniques, however, can cause disruption of the heart wall prior to release of the affixed lead tip, causing fatality, or other complications, such as lead breakage with subsequent migration, myocardial avulsion or avulsion of a tricuspid valve leaflet. Moreover, lead and electrode tip removal may further be prevented by a channel of fibrotic scar tissue and endothelium surrounding the outer surface of the lead body or insulator sleeve at least part way along the venous pathway. Such channel scar tissue inhibits withdrawal of the lead and electrode tip because they are encased within the scar tissue.

Conventional electrosurgery methods have not been successful in removing pacemaker leads. One of the factors which appears to create the greatest impediment to electrosurgical removal of pacemaker leads is scar tissue. Scar tissue exhibits much lower thermal conductivity and electrical conductivity than normal (e.g., myocardial) tissue. Since conventional electrosurgery generally relies on the conduction of electrical currents through the target tissue being cut or vaporized, conventional electrosurgery has failed to remove this scar tissue. In fact, previous attempts to use conventional electrosurgery methods to remove pacemaker leads have resulted in current flow and thermal effects in the "healthy" tissue surrounding the scar tissue mass, but not in the scar tissue mass itself. As a result, the targeted scar tissue was not affected and the lead was not removable.

What is needed is an apparatus for removing unused pacemaker leads that can relatively quickly and easily cut through the fibrotic scar tissue and endothelium surrounding the outer surface of the lead body and electrode tip and does not require additional apparatus for removal except the lead and electrode tip itself.

BRIEF SUMMARY OF THE INVENTION

It is an object of the present invention to provide a lead body and electrode tip that is relatively easy to insert It is another object of the present invention to provide a lead body and electrode tip that can be removed without being associated with serious risks.

It is yet another object of the present invention to provide a lead tip that upon removal can relatively quickly and easily cut through the fibrotic scar tissue and endothelium surrounding the outer surface of the lead body and electrode tip.

The above objects are achieved by providing an extractable endocardial tip for an electrode of an electrical stimulator having a lead body with a front end for positioning the electrode within a desired area and a back end for connecting to an electrical source. The lead body may have convexities or concavities to increase the contact surface and improve conductivity. At least one fin protrudes from the lead body. The fin has an anterior leading edge and a posterior receding edge wherein at least a portion of the posterior receding edge is serrated to form a cutting surface. The serrated edge is relatively sharp such that when the electrode is pulled, the serrated edge of the fin cuts through any fibrous scar tissue or any other inhibiting material that surrounds the electrode to facilitate the relatively easy withdraw of the electrode from the heart.

Additional objects, features and advantages will be apparent in the written description which follows.

BRIEF DESCRIPTION OF THE DRAWINGS

The novel features believed characteristic of the invention are set forth in the appended claims. The invention itself however, as well as a preferred mode of use, will best be understood by reference to the following detailed description of an illustrative embodiment when read in conjunction with the accompanying drawings, wherein:

DETAILED DESCRIPTION OF THE PREFERRED EMBODIMENT

Figure 5:
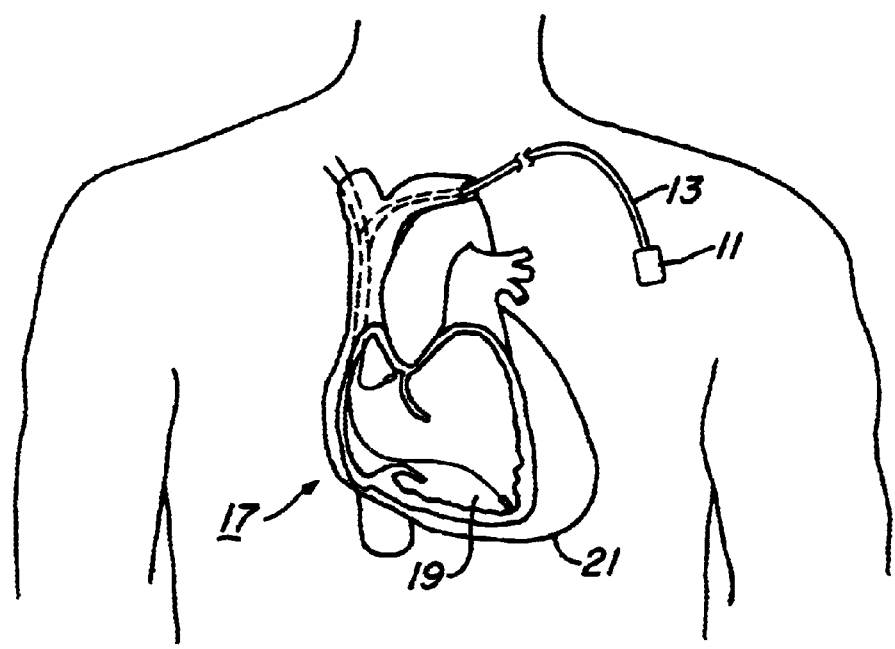
FIG. 5 is a diagram of a pacemaker with the electrode in the apex of the right ventricle and another one on the right arterial appendix.

Referring to FIG. 5, an existing electrical stimulator such as a pacemaker 11 consists of a power source and electronic circuitry which together constitute a pulse generator housed within the pacemaker 11. The pacemaker 11 is arranged to be inserted within a patients body normally near one of the pectoral muscles. An insulated lead 13 or electrical wire having a proximal end connected into a receiving port of the pacemaker 11 and a distal end connected to one or more extractable endocardial electrode tips 15. Tip 15 is located inside the patients heart 17 and provides a direct connection with the pacemaker 11 and the heart 17. Generally, the electrode tip 15 is implanted for sensing cardiac activity and providing pacing pulses. The electrode tip 15 may be substantially flush with the surface of the heart 17 to contact heart tissue to provide epicardial stimulation/sensing functions. Alternatively, the body of the electrode tip 15 may include an attachment means such as a helical screw tip, barb, or some other device for fixation to the heart or any other desired organ or area. The attachment means may be on the anterior end of the electrode tip 15. The electrode tip 15 preferably enables stimulation and sensing of cardiac tissue from the pacemaker via the lead 13. Typically, electrode 15 is positioned in the right ventricle 19 near the apex 21 of the heart 17 where the free walls of the left and right ventricles meet the intraventricular septum. By being positioned in the right ventricle 19 near the apex 21 of the heart 17, the electrodes 15 are in contact with the apical area of the heart 17 and can deliver stimulating impulses to the endocardium for pacing the apical area.

The lead 13 to the electrode tip 15 may have a curve imparted to it to aid in positioning the electrode against a desired area such as the intraventricular septum. The desired area for placement of the electrode tip 15 could also include any other area of the body where an organ needs a stimulator point or an electrical stimulator is needed.

Figure 1:
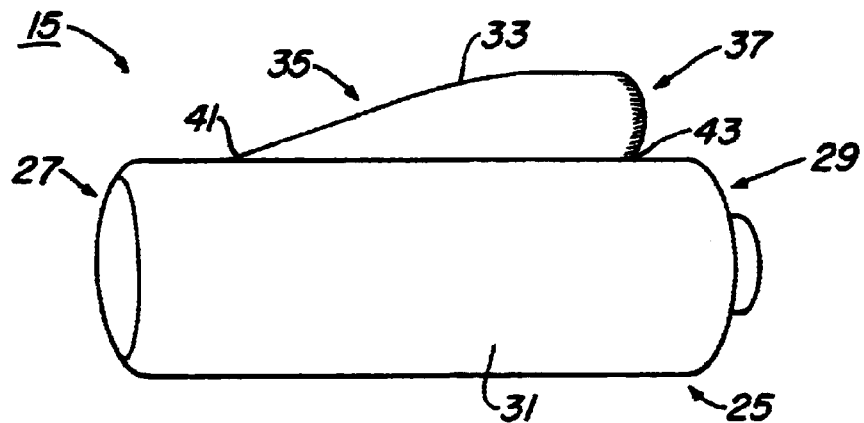
FIG. 1 is a perspective side view of an electrode tip constructed in accordance with the invention and having one fin.
Figure 2:
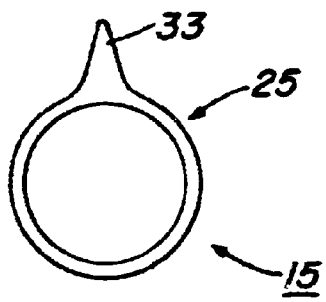
FIG. 2 is a front view of the electrode tip of FIG. 1.
Figure 3:
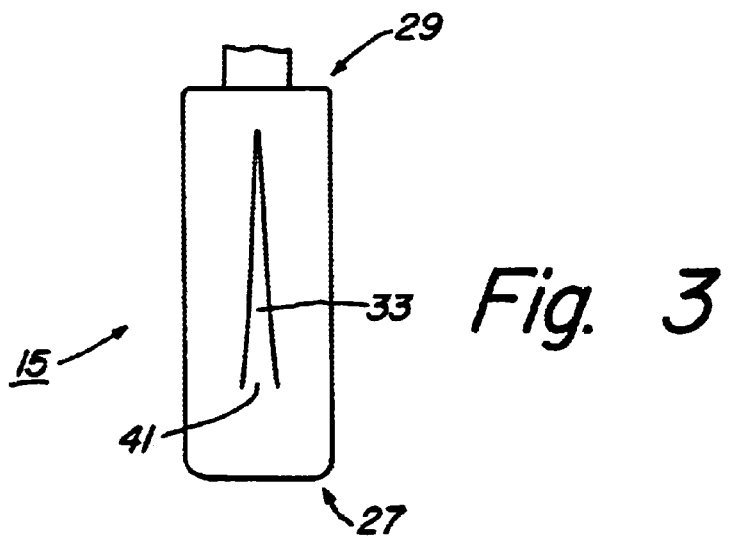
FIG. 3 is a top view of the electrode tip of FIG. 1.
Figure 6:
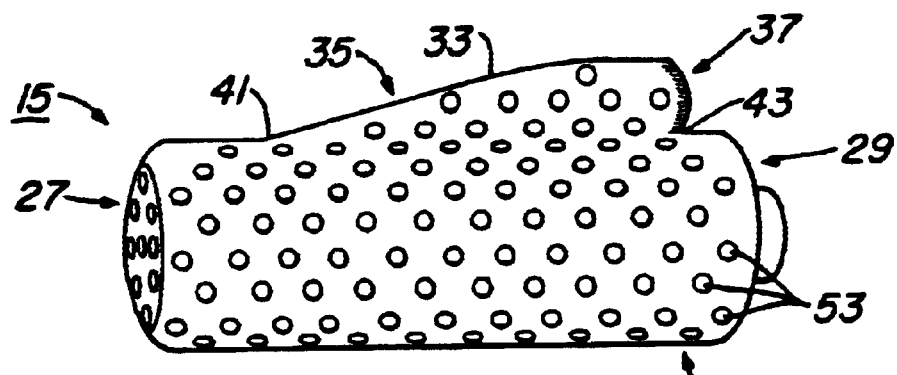
FIG. 6 is a perspective side view of an alternate embodiment of the electrode tip of FIG. 1, the exterior surface having convexities.
Figure 7:
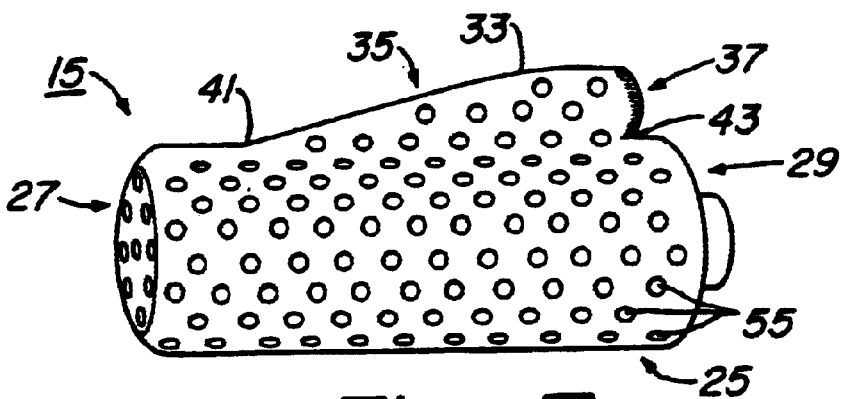
FIG. 7 is a perspective side view of another alternate embodiment of the electrode tip of FIG. 1, the exterior surface having concavities.

Referring to FIG. 1, the lead body 25 of the electrode tip 15 has a general cylindrical shape and an anterior end 27 for positioning within a desired area and a posterior end 29 for connecting to an insulated lead 13. The lead body 25 is made of physically compatible conductive material, for example micro porous platinum black or any other suitable conductive material may be deposited upon the outside surface 31. In the first embodiment, the outer surface 31 of the body 25 is smooth. However, the exterior surface of the body and fin may have irregularities as shown in FIGS. 6 and 7.

Figure 4:
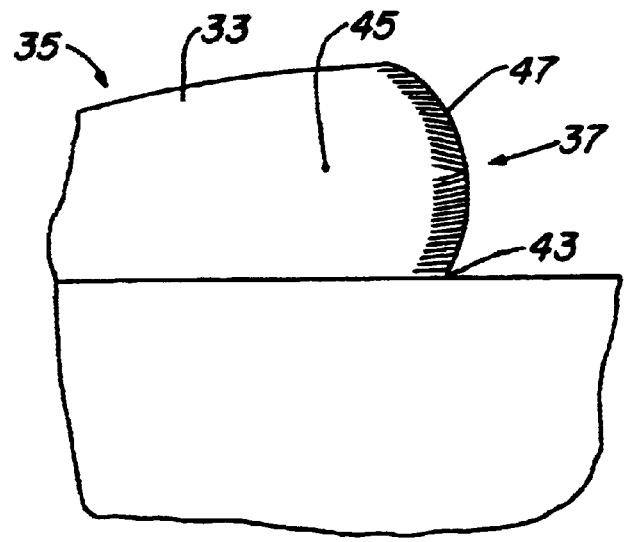
FIG. 4 is an enlarged view of the fin of the electrode tip of FIG. 1, showing a serrated edge.

The electrode tip 15 contains at least one fin 33 protruding from the body 25, to aid in fixation as well as extraction of the electrode tip 15. The fin 33 generally has an anterior leading edge 35 and a posterior receding edge 37. The anterior leading edge 35 inclines rearward and at an acute angle of generally 20 degrees relative to the longitudinal axis of the lead body 25. The anterior leading edge 35 is slightly curved outward. Leading edge 35 begins a selected distance from tip 41 and posterior edge 37 terminates a selected distance from end 43. The total length of fin 33 is about 60% the total length of the electrode tip 15. As shown in FIG. 4, fin 33 is on a radial line of the longitudinal axis of electrode tip 15. The radial extent of fin 33 is less than the radius of the body 25.

As shown in FIG. 4, the posterior edge 37 is curved in shape in a radius about a center point 45. Center point 45 is located exterior of body 25 and forward from edge 37. This provides a generally convex shape to edge 37 with the central portion being farther rearward than the inner and outer termination of edge 37. At least a portion of the posterior receding edge 37 is serrated to form a cutting edge 47 for the extraction of the electrode. The serrations may be cut at opposite angles to enhance the sharpness of the edge 47. Any general fin shape that would provide a cutting edge 47 suitable for cutting tissue surrounding the electrode tip 15 can be used. The cutting edge 47 is relatively sharp and is able to cut through any tissue or obstruction that may cover the electrode tip 15 simply by pulling on the lead 13.

The electrode tip 15 may be inserted into the heart 17 or any other organ through a venous access. The electrode tip 15 may also be inserted by cutting into the desired organ and inserting the electrode tip 15 or the electrode tip 15 may be attached to the organ by attachment means such as a screw 49 or a barb 51. During implant, the lead 13 is stiffened with a stylet, straightening the curve for insertion through an introducer sheath and through a vein. Upon removal of the stylet, or insertion of a less stiff stylet, the lead body resumes its curved shape to guide the electrode tip 15 toward the desired area. Pulling on one arm of the stylet and pushing on the other arm causes the pair to bow a sufficient amount to position the electrode tip 15. Use of this technique for steerable guide wires is known in the art. The reinsertion of the same or a similar stylet will provide the necessary strength and stiffness to actively extract the inventive lead 13 by simply pulling on the lead 13 with relatively little force. Another technique for achieving a desired insulated lead 13 curvature is disclosed in U.S. Pat. No. 4,677,990 to Neubauer, and the patent is incorporated herein by reference.

When it is time for the electrode to be withdrawn from the heart 17, a stylet is reinserted into the insulated lead 13 to stiffen the insulated lead 13 and light pressure is applied to the insulated lead 13 such that the cutting edge 47 of the fin 33 cuts through any fibrous scar tissue or any other inhibiting material that surrounds the electrode tip 15 to facilitate the relatively easy withdraw of the electrode tip 15 from the heart 17. Once the electrode tip 15 is free from the tissue or material holding it in place, the electrode tip 15 is withdrawn from the organ by simply continuing the light pressure on the insulated lead 13 until it is totally withdrawn from the patient's body. When the electrode tip 15 is coming out towards the surface, the fin 33 will cut any fibrotic tissue surrounding the insertion opening made when the electrode tip 15 was first inserted. Because the tissue surrounding the insertion opening is cut, the same hole may be used for access to the subclavian for the implantation of a new pacemaker lead 13.

The convexities 53 and concavities 55 provide an increased contact area that improves the conductivity of electrical stimuli to the heart or any other desired organ. The outer surface 31 may be covered by a biocompatible material to help facilitate tissue growth. The electrode tip 15 may be used as a subcutaneous (SQ) patch electrode or defibrillator electrode. In addition to or instead of the SQ electrode, a superior vena cava (SVC) electrode maybe used, and maybe located on the body or may be on a separate electrode tip 15. A septal pacing electrode may be used to pace the ventricles as needed, and may provide improved hemodynamics as compared with the typical method of pacing at the apex 21. Two sensing electrodes may be positioned to provide optimum clinical pacing and/or sensing. As another alternative, pairs of electrodes 15 may be used to discriminate between various arrhythmias, using the techniques of one or more of the following U.S. Patents, which are incorporated herein by reference in their entirety: U.S. Pat. No. 4,354,497 to Kahn; U.S. Pat. No. 4,790,317 to Davies; and U.S. Pat. No. 4,799,493 to DuFault.

Figure 8:
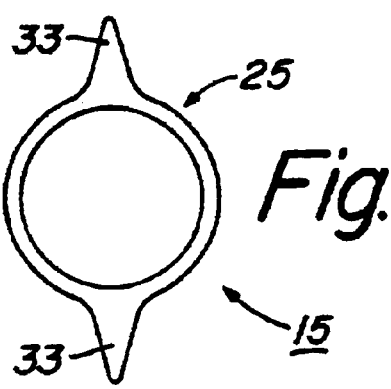
FIG. 8 is a front view of another alternate embodiment of the electrode tip of FIG. 1, the electrode tip having two fins.
Figure 9:
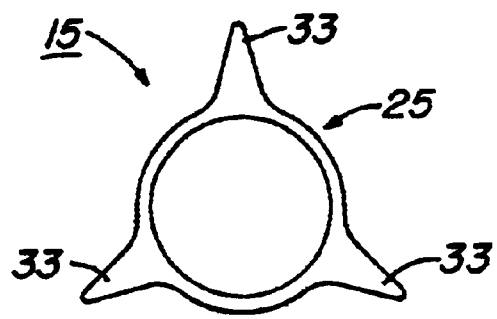
FIG. 9 is a front view of another alternate embodiment of the electrode tip of FIG. 1, the electrode tip having three fins.

Referring to FIGS. 8 and 9 the body 25 may have one, two, three or four fins 33. An extra fin increases the surface area to sense and stimulate the organ in need as well as aid in fixation and extraction. The fins 33 may be placed any distance from each other but preferably are equal distance from each other.

Fibrotic scar tissue and endothelium is particularly difficult to free the electrode tip 15 from and a common problem when trying to remove the electrode tip 15. However the present invention is able to cut through the fibrotic scar tissue for a relatively easy extraction. The fin 33 is an intrinsic part of the electrode tip 15 and provides an increased contact area to sense and stimulate the organ in need.

It should be understood that various alternatives to the embodiments of the invention described herein may be employed in practicing the invention. For example the tip 15 may have 4 or 5 fins 33. Also, the fin 33 may be the same length or less than about 60% the total length of the electrode tip 15. It is intended that the following claims define the scope of the invention and that structures and methods within the scope of these claims and their equivalents be covered thereby.

What is claimed is:

1. An extractable endocardial tip for an electrode of an electrical stimulator, the tip comprising:
a body having an anterior end for positioning within a desired area and a posterior end for connecting to an electrical wire;
at least one fin protruding from the body, the fin having an anterior edge and a posterior edge; and wherein
at least a portion of the posterior edge is serrated to form a cutting surface during extraction of the tip.

2. The tip of claim 1 wherein the serrations are cut at opposite angles to enhance the sharpness of the edge.

3. An extractable endocardial tip for an electrode of an electrical stimulator, the tip comprising:
a body having an anterior end for positioning within a desired area and a posterior end for connecting to an electrical wire;
at least one fin protruding from the body, the fin having an anterior edge and a posterior edge; and wherein
the body has outer surface with a plurality of convexities.

4. An extractable endocardial tip for an electrode of an electrical stimulator, the tip comprising:
a body having an anterior end for positioning within a desired area and a posterior end for connecting to an electrical wire;
at least one fin protruding from the body, the fin having an anterior edge and a posterior edge; and wherein
the body has outer surface with a plurality of concavities.

5. An extractable endocardial tip for an electrode of an electrical stimulator, the tip comprising:
a body having an anterior end for positioning within a desired area and a posterior end for connecting to an electrical wire;
at least one fin protruding from the body, the fin having an anterior edge and a posterior edge; and wherein
the posterior edge is sharp for cutting tissue during extraction of the tip.

6. The tip of claim 5 wherein the body has an outer surface that is smooth.

7. The tip of claim 5 wherein the body has a generally cylindrical shape and the fin extends along a radial plane of a longitudinal axis of the body.

8. The tip of claim 5 wherein said at least one fin comprises a plurality of said fins.

9. The tip of claim 5 wherein the anterior edge inclines rearward and at an acute angle relative to a longitudinal axis of the body.

10. An extractable endocardial tip for an electrode of an electrical stimulator, the tip comprising:
a body having an anterior end for positioning within a desired area and a posterior end for connecting to an electrical wire;
at least one fin protruding from the body, the fin having an anterior edge and a posterior edge; and wherein
the posterior edge of said fin is in a convex curved shape.

11. An extractable endocardial tip for an electrode of an electrical stimulator, the tip comprising:
a body having a generally cylindrical shape and having a longitudinal axis, an anterior end for positioning within a desired area, and a posterior end for connecting to an electrical wire; and
at least one fin protruding from the body, the fin having an anterior edge and a posterior edge, wherein the anterior edge inclines rearward and at an acute angle relative to the longitudinal axis, and at least a portion of the posterior edge forms a cutting surface to facilitate later extraction of the tip; and wherein
the body has an outer surface with a plurality of convexities.

12. An extractable endocardial tip for an electrode of b an electrical stimulator, the tip comprising:
a body having a generally cylindrical shape and having a longitudinal axis, an anterior end for positioning within a desired area, and a posterior end for connecting to an electrical wire; and
at least one fin protruding from the body, the fin having an anterior edge and a posterior edge, wherein the anterior edge inclines rearward and at an acute angle relative to the longitudinal axis, and at least a portion of the posterior edge forms a cutting surface to facilitate later extraction of the tip; and wherein the body has an outer surface with a plurality of concavities.

13. An extractable endocardial tip for an electrode of an electrical stimulator, the tip comprising:

a body having a generally cylindrical shape and having a longitudinal axis, an anterior end for positioning within a desired area, and a posterior end for connecting to an electrical wire; and at least one fin protruding from the body, the fin having an anterior edge and a posterior edge, wherein the anterior edge inclines rearward and at an acute angle relative to the longitudinal axis, and at least a portion of the posterior edge forms a cutting surface to facilitate later extraction of the tip; and wherein the posterior edge is sharp for cutting tissue during extraction of the tip.

14. The tip of claim 13 wherein the body has an outer surface that is smooth.

15. The tip of claim 13 wherein the anterior edge joins the body rearward of the anterior end and posterior edge joins the body forward of the posterior end.

16. A method for attaching and subsequent withdraw of an electrode from a heart muscle, the method comprising the step of:

connecting an electrode to a lead, the electrode having at least one fin protruding from the body that has a sharp cutting posterior edge;

inserting the electrode into the heart through a venous access; then to withdraw the electrode, pulling on the lead such that the sharp posterior cutting edge of the fin cuts through any fibrous scar tissue or inhibiting material surrounding the body, thereby allowing for withdraw of the electrode from the heart muscle.

17. The method of claim 16 wherein the pulling on the electrode lead continues after withdraw of the electrode from the heart muscle until the electrode is completely withdrawn from a patient's body and upon exiting the patient's body the cutting edge of the fin is used to cut an access opening for reinsertion of another lead.

* * * * *